United States Patent
Judell et al.

(10) Patent No.: US 9,526,424 B2
(45) Date of Patent: *Dec. 27, 2016

(54) APPARATUS, SYSTEMS, AND METHODS OF IN-VIVO BLOOD CLEARING IN A LUMEN

(71) Applicant: LightLab Imaging, Inc., Westford, MA (US)

(72) Inventors: Neil Judell, Cambridge, MA (US); Robert Steinbrecher, Wrentham, MA (US); Joel Friedman, Andover, MA (US); Christopher Petersen, Carlisle, MA (US)

(73) Assignee: LIGHTLAB IMAGING, INC., Westford, MA (US)

( * ) Notice: Subject to any disclaimer, the term of this patent is extended or adjusted under 35 U.S.C. 154(b) by 227 days.

This patent is subject to a terminal disclaimer.

(21) Appl. No.: 13/780,611

(22) Filed: Feb. 28, 2013

(65) Prior Publication Data

US 2013/0310698 A1 Nov. 21, 2013

Related U.S. Application Data

(63) Continuation of application No. 12/888,355, filed on Sep. 22, 2010, now Pat. No. 8,412,312.

(Continued)

(51) Int. Cl.
*A61B 5/05* (2006.01)
*A61B 5/00* (2006.01)
*A61B 5/02* (2006.01)

(52) U.S. Cl.
CPC ............ *A61B 5/0073* (2013.01); *A61B 5/0066* (2013.01); *A61B 5/02007* (2013.01); *A61B 5/6852* (2013.01); *A61B 5/7285* (2013.01)

(58) Field of Classification Search
CPC . A61B 5/0066; A61B 5/0073; A61B 5/02007; A61B 5/6852; A61B 5/7285
(Continued)

(56) References Cited

U.S. PATENT DOCUMENTS

| 5,054,492 A | 10/1991 | Scribner et al. |
| 5,321,501 A | 6/1994 | Swanson et al. |

(Continued)

FOREIGN PATENT DOCUMENTS

| WO | 2006 024015 A1 | 3/2006 |
| WO | 2006076409 | 7/2006 |
| WO | 2007002685 | 1/2007 |

OTHER PUBLICATIONS

Hariri et al., "An automatic image processing algorithm for initiating and terminating intracoronary OFDI pullback," Biomedical Optics Express, 1(2):566-573, Sep. 1, 2010.

(Continued)

*Primary Examiner* — Jonathan Cwern
(74) *Attorney, Agent, or Firm* — K&L Gates LLP (57) ABSTRACT

In one aspect, the invention relates to a computer-implemented method of triggering optical coherence tomography data collection. The method includes collecting optical coherence tomography data with respect to a vessel using an optical coherence tomography probe disposed in the vessel; determining a clearing radius and a quality value for each frame of optical coherence tomography data collected for the vessel using a computer; determining if a blood clearing state has occurred using at least one clearing radius and at least one quality value; and generating a trigger signal in response to the blood clearing state.

29 Claims, 4 Drawing Sheets

Related U.S. Application Data (60) Provisional application No. 61/244,985, filed on Sep. 23, 2009.

(58) Field of Classification Search
USPC .......................................................... 600/479
See application file for complete search history.

(56) References Cited

U.S. PATENT DOCUMENTS

| | | | |
|---|---|---|---|
| 5,459,570 A | 10/1995 | Swanson et al. | |
| 5,465,147 A | 11/1995 | Swanson | |
| 5,488,674 A | 1/1996 | Burt et al. | |
| 5,509,093 A | 4/1996 | Miller et al. | |
| 5,531,227 A | 7/1996 | Schneider | |
| 5,619,368 A | 4/1997 | Swanson | |
| 5,662,109 A | 9/1997 | Hutson | |
| 5,748,598 A | 5/1998 | Swanson et al. | |
| 5,771,895 A | 6/1998 | Slager | |
| 5,784,352 A | 7/1998 | Swanson et al. | |
| 5,797,849 A | 8/1998 | Vesely et al. | |
| 5,956,355 A | 9/1999 | Swanson et al. | |
| 5,989,189 A | 11/1999 | LeBlanc et al. | |
| 6,111,645 A | 8/2000 | Tearney et al. | |
| 6,134,003 A | 10/2000 | Tearney et al. | |
| 6,148,095 A | 11/2000 | Prause et al. | |
| 6,160,826 A | 12/2000 | Swanson et al. | |
| 6,191,862 B1 | 2/2001 | Swanson et al. | |
| 6,208,883 B1 | 3/2001 | Holupka et al. | |
| 6,282,011 B1 | 8/2001 | Tearney et al. | |
| 6,421,164 B2 | 7/2002 | Tearney et al. | |
| 6,445,939 B1 | 9/2002 | Swanson et al. | |
| 6,485,413 B1 | 11/2002 | Boppart et al. | |
| 6,501,551 B1 | 12/2002 | Tearney et al. | |
| 6,552,796 B2 | 4/2003 | Magnin et al. | |
| 6,564,087 B1 | 5/2003 | Pitris et al. | |
| 6,570,659 B2 | 5/2003 | Schmitt | |
| 6,706,004 B2 | 3/2004 | Tearney et al. | |
| 6,879,851 B2 | 4/2005 | McNamara et al. | |
| 6,891,984 B2 | 5/2005 | Petersen et al. | |
| 7,022,073 B2 | 4/2006 | Fan et al. | |
| 7,208,333 B2 | 4/2007 | Flanders et al. | |
| 7,231,243 B2 | 6/2007 | Tearney et al. | |
| 7,241,286 B2 | 7/2007 | Atlas | |
| 7,312,879 B2 * | 12/2007 | Johnston | 356/614 |
| 7,414,779 B2 | 8/2008 | Huber et al. | |
| 7,415,049 B2 | 8/2008 | Flanders et al. | |
| 7,593,559 B2 | 9/2009 | Toth et al. | |
| 7,610,081 B2 | 10/2009 | Redel | |
| 7,625,366 B2 | 12/2009 | Atlas | |
| 7,729,746 B2 | 6/2010 | Redel et al. | |
| 7,813,609 B2 | 10/2010 | Petersen et al. | |
| 7,848,791 B2 | 12/2010 | Schmitt et al. | |
| 7,916,387 B2 | 3/2011 | Schmitt et al. | |
| 7,935,060 B2 | 5/2011 | Schmitt et al. | |
| 8,208,995 B2 | 6/2012 | Tearney et al. | |
| 2002/0115931 A1 | 8/2002 | Strauss et al. | |
| 2002/0161351 A1 | 10/2002 | Samson et al. | |
| 2005/0201662 A1 | 9/2005 | Petersen et al. | |
| 2006/0058622 A1 * | 3/2006 | Tearney et al. | 600/407 |
| 2006/0095065 A1 | 5/2006 | Tanimura et al. | |
| 2006/0165270 A1 | 7/2006 | Borgert et al. | |
| 2006/0203859 A1 | 9/2006 | Cable et al. | |
| 2006/0241465 A1 | 10/2006 | Huennekens et al. | |
| 2006/0244973 A1 | 11/2006 | Yun et al. | |
| 2007/0078500 A1 * | 4/2007 | Ryan et al. | 607/88 |
| 2007/0167710 A1 | 7/2007 | Unal et al. | |
| 2007/0167833 A1 * | 7/2007 | Redel et al. | 600/476 |
| 2008/0100612 A1 | 5/2008 | Dastmalchi et al. | |
| 2009/0306520 A1 | 12/2009 | Schmitt et al. | |
| 2010/0076320 A1 | 3/2010 | Atlas et al. | |
| 2010/0094127 A1 | 4/2010 | Xu | |
| 2010/0253949 A1 | 10/2010 | Adler et al. | |
| 2011/0007315 A1 | 1/2011 | Petersen et al. | |
| 2011/0071404 A1 | 3/2011 | Schmitt et al. | |
| 2011/0071405 A1 | 3/2011 | Judell et al. | |
| 2011/0101207 A1 | 5/2011 | Schmitt | |
| 2011/0151980 A1 | 6/2011 | Petroff | |

OTHER PUBLICATIONS

PCT Notification of Transmittal of the International Search Report and the Written Opinion of the International Searching Authority for PCT Patent Application No. PCT/US2010/049891, mailed Nov. 30, 2010 (9 pgs.).

English translation of Japanese Office Action for Japanese Divisional Application No. 2014-221904, mailed on Nov. 4, 2015 (2 pages).

* cited by examiner

APPARATUS, SYSTEMS, AND METHODS OF IN-VIVO BLOOD CLEARING IN A LUMEN

CROSS-REFERENCE TO RELATED APPLICATIONS

This application is a continuation of U.S. patent application Ser. No. 12/888,355, filed on Sep. 22, 2010, which claims priority to U.S. Provisional Patent Application Ser. No. 61/244,985 filed Sep. 23, 2009, the entire disclosure of which is incorporated by reference herein.

FIELD OF THE INVENTION

The present invention relates to the field of in-vivo data collection and, in particular, to optical coherence tomography.

BACKGROUND

Optical Coherence Tomography (OCT) is a promising diagnostic imaging technology that utilizes advanced photonics and fiber optics to obtain cross-sectional tomographic images on a microscopic resolution scale. The technology has the potential to dramatically change the way physicians, researchers and scientists see and understand the human body in order to better diagnose and treat disease. OCT combines the principles of ultrasound with the imaging performance of a microscope and a form factor that is familiar to clinicians.

Whereas ultrasound produces images from backscattered sound "echoes," OCT uses infrared light waves that reflect off the internal microstructure within the biological tissues. The frequencies and bandwidths of infrared light are orders of magnitude higher than medical ultrasound signals resulting in greatly increased image resolution; about 8-25 times greater than ultrasound or x-ray based modalities. OCT uses coherence-gating to detect singly-scattered photons thereby permitting tomographic imaging similar to ultrasound or computed tomography (X-ray), but at much higher resolution. While standard electronic techniques are adequate for processing ultrasonic echoes that travel at the speed of sound, interferometric techniques are required to extract the reflected optical signals from the light used in OCT. The output, measured by an interferometer, is computer processed to produce high-resolution, real time, cross sectional or 3-dimensional images of the tissue. This powerful technology provides in situ images of tissues at near histological resolution without the need for excision or processing of the specimen.

For example, imaging of coronary arteries by intravascular OCT may reveal the location of a stenosis, the presence of vulnerable plaques, or the type of atherosclerotic plaque. This information helps cardiologists to choose which treatment would best serve the patient—drug therapy (e.g., cholesterol-lowering medication), a catheter-based therapy like angioplasty and stenting, or an invasive surgical procedure like coronary bypass surgery.

One of the fundamental limitations of cardiovascular OCT is that it cannot image through blood because the components of red blood cells strongly scatter the near-infrared light, making image reconstruction impossible. As a result, there is a need for systems, methods, and apparatus that facilitate and detect blood clearing in a lumen. The aspects and embodiments of the invention discussed below addresses this need.

SUMMARY OF THE INVENTION

In general, the invention provides various methods, systems, and apparatus to facilitate blood clearing such that OCT data collection can occur. As outlined below, the process of collecting OCT data is time sensitive. Typically, a catheter that includes an OCT probe is introduced into a lumen of interest. The probe typically includes a rotating or slidable fiber that directs light forward into the lumen or at a direction perpendicular to the longitudinal axis of the fiber. As a result, in the case of light that is directed from the side of the fiber as the fiber rotates, OCT data is collected with respect to the walls of a lumen. Further, as the fiber is retracted (pulled-back) along the length of the vessel, a plurality of scans or OCT data sets are collected as the fiber rotates. In one embodiment, this is referred to herein as a pullback. These data sets can be used to identify regions of interest such as locations where a stent should be placed or where a procedure should be undertaken. A three-dimensional image or a two dimensional cross section of a given lumen can be generated using the data collected using an OCT probe and associated OCT subsystems or components.

As discussed above, OCT data cannot easily be collected in the presence of blood. Accordingly, embodiments of the invention provide solutions relating to flushing blood from the lumen and triggering OCT data collection when the lumen is sufficiently clear of blood.

One feature of an embodiment of the invention is to place no additional requirements, other than proper catheter placement in the artery and injection of the flush, on the operator of the OCT system. Thus, in one embodiment, additional hardware (pressure transducer or flush pump trigger) is not required to perform the procedure. Accordingly, the OCT system operator is not required to visually determine when the flush has cleared the artery and manually trigger the system to begin the pullback. From the system operator's point of view, once the flush has been injected, the OCT system will automatically create a pullback recording of the cleared artery.

Another feature of an embodiment of the invention is to reduce the amount of computer or processor processing time to detect flush clearing in a OCT data set or image. In part, this computer-based method processes OCT data in real time and does not interrupt the OCT data acquisition such as during a pullback. Images are typically acquired at a rate of about 100-200 frames per second (100-200 Hz), leaving less than about 5-10 milliseconds of real time processing time to acquire and process the image. These temporal limits require an exemplary embodiment of a flush clearing detection method to spend less than about 3 milliseconds (0.003 s) processing each image frame which can contain upwards of 500,000 pixels. However, this limit can change by using fewer images. In some embodiments, reference to images and OCT data are included. The system and methods described herein can process raw data directly or images formed therefrom in various embodiments.

Another feature of an embodiment of the invention is to provide several parameters that may be modified to change the behavior of the flush clearing detection method. The default values of these parameters are determined by performing the computer-based method on a group of previously obtained OCT image sequences or data sets in which the first fully clear frame was determined through human inspection. The values of these parameters that produce the best results of the software trigger occurring at or near this first full clear frame across all recordings can be set as the default values. Thus, the system can be trained using successful clearing data sets and images. By using historic OCT data obtained during clearing states to train an automatic system, error is reduced and the ease of obtaining OCT data increases.

In one embodiment, initial border location of the lumen of interest is sufficient for detecting the radius of the clearing. In part, embodiments of the invention also do not require a precise level of edge detection to achieve suitable levels of blood clearing to trigger data collection. Therefore, computationally simpler computer-based methods may be used.

A computer-implemented method of triggering optical coherence tomographic data collection in a length of a vessel is also provided. The method can include collecting optical coherence tomography data with respect to a location in the vessel using an optical coherence tomography probe disposed in the vessel, determining a parameter indicative of blood clearing for one or more frames of optical coherence tomography data collected for the vessel using a computer, determining if a blood clearing state has occurred using the parameter, and generating a trigger signal in response to the blood clearing state. The method can also include the step of triggering longitudinal optical coherence tomography data collection in response to the trigger signal. Optionally, a time delay timeout can occur prior to commencing longitudinal optical coherence tomography data collection. In some embodiment, the parameter is selected from the group consisting of vessel wall scattering, a vessel quality value, a vessel clearing radius, a plurality of vessel intensity values, LineRadius, quality metric, clearing radius, quality value, full clear frame and initial clear frame.

In some embodiments, the step of determining the parameter is performed using at least one intensity value or at least one intensity-derived position such that the intensity value is correlated with a boundary of the vessel. In some embodiments, the at least one intensity value represents a position of a centroid of an intensity distribution along each radial line in at least one image generated from the optical coherence tomography data. In some embodiments, the position of the centroid is within a wall of the vessel. The computer-implemented method can also include the step of determining a centroid of an intensity distribution such that intensity data occurring within a catheter sheath is excluded. Optionally, using a computer, the centroid is approximated as a first moment of the intensity distribution. In some embodiments, the position of the centroid can be determined using a computer performing the step of fitting a function of a plurality of radii using a series comprising sine and cosine functions. In addition, a maximum or minimum clearing radius can be determined using the series. In some embodiments, the clearing radius is determined by detecting scattering from a wall of the vessel. In some embodiments, the quality value is a determined using scattering about a detected clear area of the vessel and the clearing radius. In some embodiments, the quality factor is determined using a computer by a ratio of an intensity-position variance and maximum clear radius. In some embodiments, the parameter is a quality metric determined using a computer by a ratio of an intensity standard deviation and maximum clear radius. In some embodiments, the parameter is a quality metric determined using a computer by comparing a second moment of the intensity distribution to a first moment of the intensity distribution.

In addition, a computer system for triggering optical coherence tomography data collection is provided. The computer system can include an electronic memory device and an electronic processor in communication with the memory device. The memory device includes instructions that when executed by the processor cause the processor to: collect optical coherence tomography data with respect to a vessel, determine a clearing radius for each frame of optical coherence tomography data collected for the vessel, determine if a blood clearing state has occurred using the clearing radius, and generate a trigger signal in response to the blood clearing state. In some embodiments, the instructions further cause the processor to initiate optical coherence tomography data collection and pullback of the optical coherence probe in response to the trigger signal. In some embodiments, the instructions further cause the processor to initiate a pullback of the optical coherence probe through the vessel. In some embodiments, the processor determines the clearing radius using at least one intensity value such that the intensity value is correlated with a boundary of the vessel. In some embodiments, the processor determines the clearing radius using scattering of light from a wall of the vessel. In some embodiments, the blood clearing state is determined by detecting an initial clearing state or a full clearing state.

In addition, an optical coherence tomography data collection system is provided. The system can include a processor and an optical coherence tomography probe, the probe including a rotatable optical fiber, wherein the processor is programmed to trigger a pullback of the optical coherence tomography probe through a vessel in response to a blood clearing state determined by the processor based on a blood clearing parameter. In some embodiments, the blood clearing parameter is selected from the group consisting of vessel wall scattering, a vessel quality value, a vessel clearing radius, a plurality of vessel intensity values, LineRadius, and quality metric. In some embodiments, the blood clearing parameter is a clearing radius determined in response to an intensity of a wall of the vessel. In some embodiments, the processor collects data from the rotatable optical fiber during at least a portion of the pullback. In some embodiments, the vessel is a coronary artery. In some embodiments, the processor is programmed to initiate the pullback if a quality metric has reached a predetermined threshold. In some embodiments, the processor determines if the blood clearing state has occurred on a frame by frame basis.

BRIEF DESCRIPTION OF THE DRAWINGS

These embodiments and other aspects of this invention will be readily apparent from the detailed description below and the appended drawings, which are meant to illustrate and not to limit the invention, and in which.

DETAILED DESCRIPTION

Prior to discussing various embodiments of the invention, it is helpful to provide an outline of certain features of this application. For example the use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

Figure 1A:
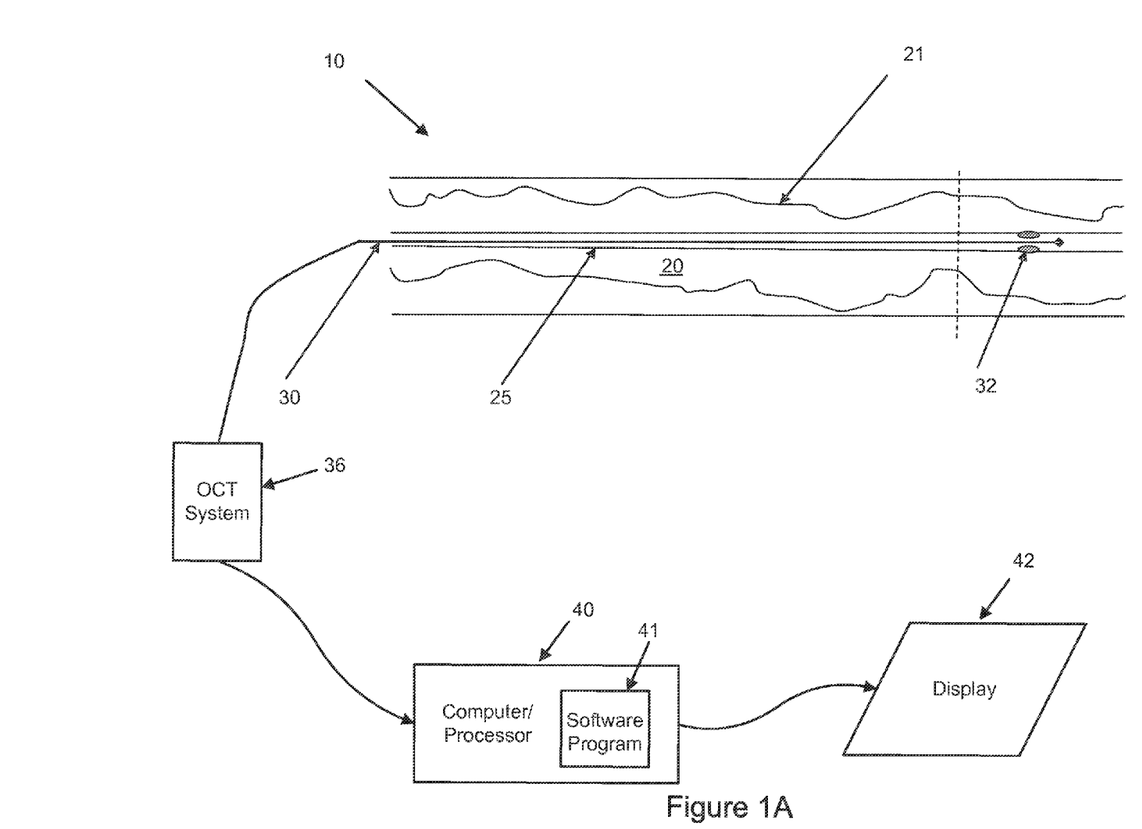
FIG. 1A is a generalized schematic of an OCT data collection system having an imaging probe disposed in a vessel of interest.

FIG. 1A is a high level schematic diagram depicting components of an OCT system 10. The OCT system 10 can include any suitable light source that satisfies the coherence and bandwidth requirements of the applications and data collection described herein. FIG. 1A is highly generalized and not to scale. A vessel or lumen of interest 20 having a vessel wall 21 is imaged using catheter 25 having a catheter portion having an optical fiber-based imaging probe 30 disposed therein. The catheter 25 includes a flushing subsystem having flush ports 32. The flushing system can be of any suitable type or variety that displaces a sufficient amount of blood such that in vivo OCT data collection can proceed using the probe 30. The system 10 includes an OCT system or subsystem 36 that connects to the imaging probe 30 via an optical fiber. The OCT system or subsystem 36 can include a light source such as a laser, an interferometer, various optical paths, a clock generator, photodiodes, and other OCT system components.

A computer or processor can be part of the OCT system 36 or can be included as a separate subsystem 40 in communication with the OCT system 36. The computer or processor 40 can include memory, storage, buses and other components suitable for processing data and executing a flush process or a software triggering method for lumen detection and pullback data collection as discussed below. In one embodiment, the computer or processor includes software implementations or programs 41 of the methods described herein that are stored in memory and executed using a processor. A display 42 can also be part of the overall system 10 for showing cross-sectional scan data as longitudinal scans or in other suitable formats.

One of the fundamental limitations of cardiovascular OCT is that it cannot image through blood because the components of red blood cells strongly scatter the near-infrared light, making image reconstruction impossible. Therefore, the lumen 20 must be temporarily cleared of blood for the period that the imaging will take place. Displacing the blood via a flush solution such as saline applied through the port 32 is possible, but the flush rate must be sufficient to overcome the native flow, which in coronary arteries is relatively high, 1-5 ml per second. In one embodiment, about 3 to about 5 seconds of clear image time can be established with flush-based approaches.

The amount of clearing time that can be established for a typical bolus (10-20 ml), is dependent on many factors such as the local blood flow rate, arterial size/imaging location, prevalence of side-branches, etc. However, it is typically in the range of about 2 to about 5 seconds. The amount of time to acquire an OCT pullback recording (OCT data collection process) is in the range of about 2 to about 4 seconds. Accordingly, it is desirable that the OCT data acquisition during the pullback is initiated the moment sufficient clearing has been established.

In a preferred embodiment, it is desirable for a computer-based method to process the scanned images in substantially real time (or other OCT system specified time period suitable for a given application) and trigger the pullback when sufficient clearing has been detected. The computer system 40 can execute the methods described herein. In one embodiment, the methods and system described herein analyze up to about 150 frames/sec of complex image data in real-time. In addition, the embodiments use one or more criterion for determining sufficient clearing. Further, embodiments of the invention are designed to work in an environment where the actual lumen shape and size is unknown. Suitable methods of detecting the flush clearing on a reliable and real-time basis using an automated software-based system or method is one feature of this invention.

In one embodiment, software detection of lumen or vessel flush clearing is initial performed as outlined below such as using all or a subset of the steps in FIG. 1B. Once a suitable clearing state is achieved the software automatically triggers the acquisition of an OCT intravascular pullback data collection process or recording. One embodiment of the invention is a software-based method used to detect the clearing status of the artery. This computer-based method processes OCT images of the artery in substantially real time to determine a clearing radius metric and quality metric value for each image. When the clearing radius and quality metric value meet the predefined "clear artery" criteria then the pullback and data acquisition starts. In one embodiment, pullback refers to when the probe 30 and/or catheter 25 is pulled back through a lumen 20 to collect data of the lumen. As the probe 30 and/or catheter 25 is pulled back OCT data is collected and sent to the OCT system 36 and/or the computer system 40. When the probe 30 is longitudinally stationary, data is sent to the computer system to execute a clear state detection method following initialization of a flush.

For example, with respect to FIG. 1A, if the lumen of interest 20 is a coronary artery, OCT imaging of the coronary artery is performed using an OCT fiber optic imaging catheter such as catheter 25 with probe 30. The OCT imaging catheter 25 is placed in the artery at the location where a pullback recording is to be started and the OCT software computer-based method flush clearing detection is initialized (enabled). The operator of the OCT system will then inject a clearing medium (flush) such as (saline, contrast solution, dextran or equivalents) into the artery to clear it for imaging. The flush clearing detection method executing on the computer 40 will then determine when the injected flush has provided sufficient clearing in the artery to allow the OCT system to acquire a good image. The pullback will be triggered by the computer when such a determination has been made. In one embodiment, the determination of sufficient clearing is made in real time by processing each frame as it is acquired by the OCT system 36 or computer system 40.

Figure 1B:
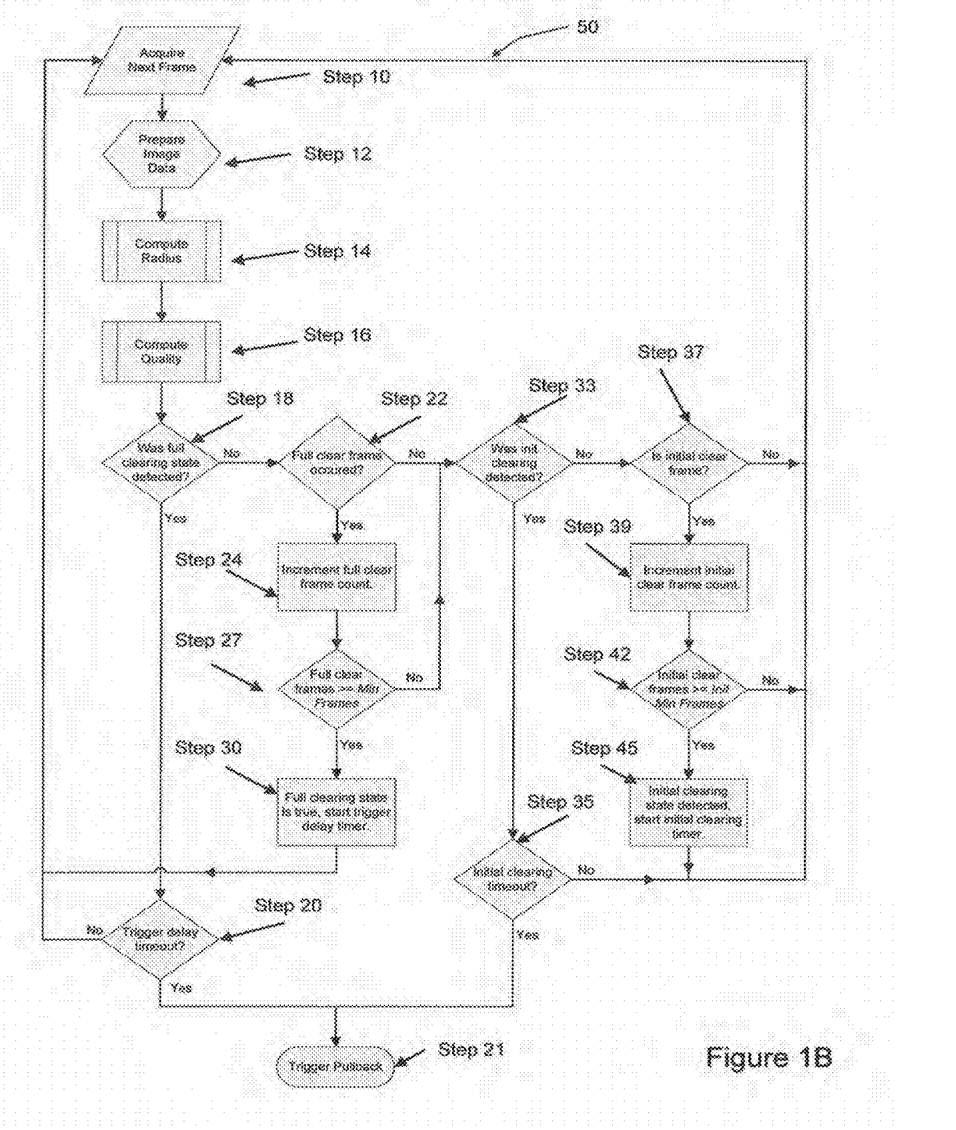
FIG. 1B is a flow chart outlining a software-based method to detect blood clearing according to an illustrative embodiment of the invention.

An exemplary method 50 for flush clearing detection and triggering a pullback and OCT data collection (and various related steps) is shown in FIG. 1B. In one embodiment, the flush clearing detection steps of method 50 assume the following unique characteristics of a clear or unclear artery in an OCT image in which the background noise has been removed:

(1) A clear vessel, such as an artery, contains scattering from the artery wall and somewhat beyond the wall. Also, the distribution of scattering about the artery wall at each angle should be localized near the wall, extending into the tissue a characteristic length determined by the physics of OCT imaging (i.e. single-scattering coherence-gated image reconstruction).

(2) A fully unclear vessel yields a small effective radius due to the presence of blood around the catheter.

(3) A partially clear vessel has a blood distributed between the catheter and the vessel wall that reduces the effective radius, and shows significant distribution of scattering away from the vessel wall, again determined by the characteristics of OCT imaging Given these assumptions this computer-based method decides if the artery is clear by first determining the value of two metrics, which will be used in the decision. These unique image attributes also allow highly efficient calculations to be completed where such calculations would not be effective with other imaging modalities. The first metric, called the radius metric, is the maximum radius in micrometers across all angles of the detected clear area of the artery. These angles correspond to the 360 degrees of angles that the OCT probe rotates through while collecting OCT data. This detected clear area is the detected radius across all angles fitted to remove expected minor obstructions (stent, guide-wire, etc.) and produce a smoothed contour.

The second metric, called the quality metric, is an indication of the quality of the clearing. It determines the average distribution of scattering about the detected clear area divided by the radius value. The unit for this metric is dimensionless, and as the actual quality of the clearing improves this value decreases (a smaller quality metric value means better clearing).

Once the values of these two metrics have been calculated they are used to determine if one of two blood clearing states has been achieved: initial clearing state means that some flush clearing has been detected and if full clearing state is not detected within a specified timeout then the pullback will be triggered; and full clearing state, in one embodiment, means that the artery is sufficiently clear and imaging can begin, the pullback will be triggered immediately or after a specified delay, if defined. Two parameters are defined as the minimum requirements for each of these two clearing states: minimum radius is the required minimum value for the radius metric; and maximum quality is the required maximum value for the quality metric. Clearing state and blood clearing state are referred to interchangeably herein. Thus, a full clearing state and an initial clear state are both non-limiting examples of a blood clearing state.

A third parameter used to determine the current clearing state is minimum frames, which specifies the minimum number of consecutive frames that must meet the minimum radius and maximum quality requirements of the clearing state before that clearing state has been achieved.

Figure 1C:
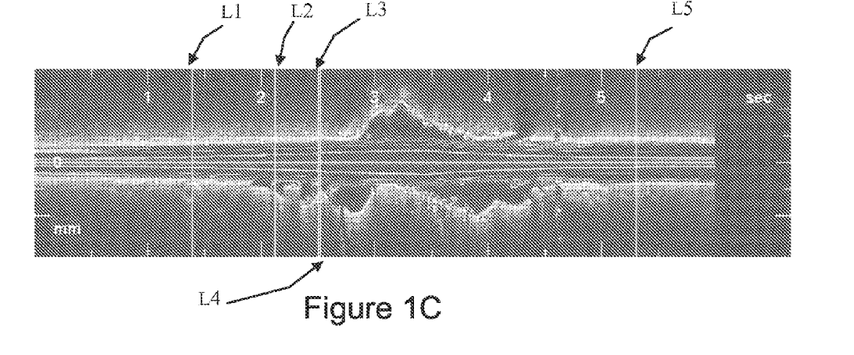
FIG. 1C is a longitudinal view of a lumen generated using an OCT probe in which the horizontal scale is shown in seconds according to an illustrative embodiment of the invention.

FIG. 1C is a longitudinal view of a lumen generated using an OCT probe in which the horizontal scale is shown in seconds according to an illustrative embodiment of the invention. As shown in the figure, there are five vertical lines that were drawn to represent various events that occurred during the recording or OCT data collection process. The L1 line indicates that the initial clearing state (discussed below) is detected approximately 1.4 seconds into the data collection process/OCT scan or recording. The L2 line indicates that the full clearing state (discussed below) is detected after 2.1 seconds. The L3 line shows when the pullback was triggered, about 2.5 seconds, which is 0.4 seconds (the trigger delay) after the full clearing state was detected. The L3 line is followed immediately by an L4 line which indicates when the pullback actually started. An L5 line, at about 5.3 seconds, indicates where the pullback ended. This FIG. 1C provides context for the concepts discussed below relating to detecting a blood clearing state in a lumen or vessel and triggering one or both of OCT data collection and a pullback sequence by which the probe is pulled back through the lumen or vessel.

As introduced above, FIG. 1B is a flow chart outlining, in part, an exemplary flush clearing detection method 50. As shown in FIG. 1B, in one embodiment, the initial step is to acquire the first or the next frame of OCT data (Step 10), such as one or more image data frames. Next, the image data is prepared in one embodiment, as outlined below (Step 12). The quality metric and radius parameters discussed above are also computed (Steps 14 and 16). The next steps in the process of FIG. 1B include various nested loops and decision trees that can be regulated using a software implementation.

For example as shown in FIG. 1B, the frame or collected OCT data is evaluated to determine whether or not a full clearing state was detected (Step 18). If the answer is "yes" the next step is to determine if the trigger delay timeout has occurred (Step 20). In one embodiment, "trigger delay timeout" occurs when the trigger delay timer expires. If it has not, the process keeps acquiring frames and returns to Step 10. If the trigger delay timeout has occurred, a pullback is triggered (Step 21).

Returning to Step 18, if a full clearing state was not detected, the process flow starting with Step 22 commences, such a determination is made if a full clear frame is detected or has occurred. In one embodiment, full clear frame is detected or occurs when the radius metric for the frame is greater than or equal to the minimum radius; and the quality metric for the frame is less than or equal to the maximum quality. However, other states for full clear frame can be used in various embodiments. Similarly, in one embodiment, full clearing state as described herein or otherwise defined in a given software embodiment occurs or is signaled when the number of consecutive frames that meet the full clear frame criteria is equal to the minimum frames.

With respect to Step 22, if the answer is "yes," than the initial clear frame count is incremented (Step 24). Again, in the case where the initial clear frame count has been incremented, after such an incrementing step, the next step is to determine if the number of full clear frames meets or exceeds the initial minimum frames parameter (Step 27). If the condition of Step 27 is satisfied, the step "full clearing state is true" and start a trigger delay timer Step 30 is started. The system then continues to "acquire the next frame" Step 10. As was the case previously, from Step 20 either a pullback will be triggered (Step 21) or an additional frame will be acquired (Step 10).

If a full clear frame is not detected in Step 22, the next step is evaluate whether or not an initial clearing state was detected (Step 33). If the answer is "yes" indicating that an initial clearing state was detected, the next step is to determine if an initial clearing timeout has occurred (Step 35). As discussed below, in one embodiment, the initial clearing timeout is the period that is started when an initial clearing state is detected such that if full clearing is not detected within that period then the pullback will be triggered. If this timeout has occurred, the process flow continues to Step 21 and a pullback is triggered. In contrast, if during Step 33, no initial clearing state has been detected, the process 50 continues to determine if the frame being evaluated is an initial clear frame (Step 37). If there is no initial clear frame, the process returns to Step 10 to evaluate the next frame. However, if there is an initial clear frame in Step 37 the next step is to increment the initial clear frame count (Step 39). Next, a determination is made as to whether the number of initial clear frames is greater than or equal to an initial minimum number of clear frames (Step 42). If is not, the process continues with Step 10. Yet, if the initial number of clear frames exceeds or meets the threshold number of initial minimum frames an initial clearing state is deemed detected. As a result, an initial clearing timer, which is longer than the trigger delay timer, is started (Step 45). The process then continues with Step 10 acquiring the next frame. If the initial clearing timeout occurs, when the initial clearing timer expires, pullback is triggered. The purpose of this is to assure that pullback will occur even in the event of suboptimal clearing, as a backup measure. In one embodiment, during such a situation a pullback can be triggered is upon the occurrence of the initial clearing timeout when the initial clearing timer has expired. Having discussed FIG. 1B in some detail, it is useful to consider other embodiments relating to OCT data triggering in response to clearing states in a lumen of interest.

Configuration

In one embodiment, the methods described herein have several configurable parameters that may be used to alter the performance of the methods described herein to produce results of interest to the operator. Some of these parameters are referenced in FIG. 1B. These include:

Boxcar size, the boxcar depth, in number of frames, to be used to perform frame averaging of the image data. In one embodiment, the values can include: 1; 2; 4; and 8. However, other values can be used or this feature can be disabled.

Max quality, the maximum quality metric allowed for a clear frame in one embodiment. This parameter is dimensionless (smaller value indicates better clearing). Two max quality values are used as input: Init Max Quality, to describe the initial clearing or initial clearing state; and max quality, to describe full clearing or full clearing state (used interchangeably herein) in one embodiment.

Min radius, the minimum radius metric value allowed for a clear frame in one embodiment. Value is typically in microns and indicates the minimum radius outside the catheter radius (described below). In one embodiment, two min radius values are used as input: init min radius, to describe the initial clearing; and min radius, to describe the full clearing in one embodiment.

Min frames, the minimum number of consecutive frames with a quality metric value less than max quality and a radius metric greater than min radius before the clearing will be triggered in one embodiment. In one embodiment, two min frames values are used as input: init min frames, used for initial clearing; and min frames, used for full clearing.

Initial clearing timeout, the amount of time, in milliseconds or another temporal unit, after the initial clearing has been detected, that detection of the full clearing will continue in one embodiment. If the full clearing is not detected within this time period, the pullback will be triggered. See Step 35 of FIG. 1B for an exemplary application of this timeout.

Trigger delay is the amount of time, in milliseconds or another temporal unit, which is to elapse after the full clearing state is detected but before the pullback is triggered. In one embodiment, the trigger delay setting in the software or program embodiment of the method is used to set the trigger delay timeout period.

Initialization

In one embodiment, when the computer-based method of detecting a clearing state is initialized the values of the following two parameters are determined. These are the catheter radius and median value. In one embodiment, the catheter radius in sample images or data sets is calculated as the physical catheter size plus 15%. In one embodiment, no image data closer than this radius will be considered for clearing. Thus, a buffer volume that extends around the catheter itself is ignored when making a determination with respect to clearing state.

In addition, the computer determines a background constant or median value, for the first frame. Typically, the computer generates the median value by generating a histogram of the image data for that frame. In this case, the median value will also be the OCT instrument (or system) 'noise floor' in one embodiment. The instrument includes the optical system and electronics, the optical coupler unit between the optical system and the catheter, and the optical catheter. The noise floor includes residual electronic noise, and optical noise created by the non-coherent light and returned light such as intensity noise and shot noise. Since the first frame, by definition, is not cleared, the image near the catheter will be dominated by blood scattering. However, the OCT intensity (coherent signal) in this case declines rapidly with distance, so that at over about 100 or about 200 um the noise floor will be reached. Further, since the scan range is approximately about 5 mm (5000 um) the median value in this frame will be the noise floor.

Preparation

As each frame is acquired, the image data for that frame is prepared for processing by a flush clearing detection method such as that shown in FIG. 1B. The purpose of this data preparation is to reduce the amount of data and simplify the processing procedure because the resolution required to detect a clearing state is less than the resolution for imaging. To reduce the amount of data, the image samples per line and lines per frame will be reduced. For example, in one embodiment, if there are more than 640 samples per line the samples will be reduced by a factor of 4, otherwise the samples will be reduced by a factor of 2; and the lines per frame will be reduced by a factor of 2. Other data processing and extraction of unnecessary data can be applied as necessary.

If the boxcar size parameter is greater than 1, then the image data is included in a running boxcar average. The boxcar size is used as the frame depth of the averaging, new frames are added to the averaging, and as the number of frames included in the average exceeds the frame depth the oldest frames are subtracted. This averaging is performed on a sample by sample basis in one embodiment.

For one embodiment of a method for detecting a clearing state and/or triggering on the same, four distinct scattering sources are assumed: red blood cells, "clear liquid", stent strut and artery wall. The stent strut is assumed to be either near the artery wall, or will subtend a very small angle or both.

Ideally, for clearing a vessel, "clear liquid", stent strut and artery wall will be the only scattering factors. The scattering intensity for "clear liquid" is the median value for frame 1, which is the instrument noise floor as determined above. This value can be subtracted from all subsequent frames to compensate for background. This results in an Intensity value for each sample:

Intensity=max(0,Sample−Median)

In one embodiment, image data inside the catheter radius is ignored or zeroed out as the Intensity is calculated. In a cleared frame, scattering from the artery wall and somewhat beyond the wall should be viewable. By measuring the radius to the vessel wall as a function of angle, it should form a fairly smooth curve. Additionally, for a cleared artery, the distribution of scatter about the vessel wall radius at each angle should be fairly small. For a fully uncleared vessel, there are red blood cells very close to the fiber, yielding a small effective radius. For a partly cleared vessel, there are red blood cells distributed between the fiber and the vessel wall, reducing the effective radius a bit, but showing significant distribution of scattering away from the artery wall. As a result, the software-based method computes two metrics for the image, the effective artery radius metric, and the clearing quality metric.

Compute Radius Metric

Figure 2:
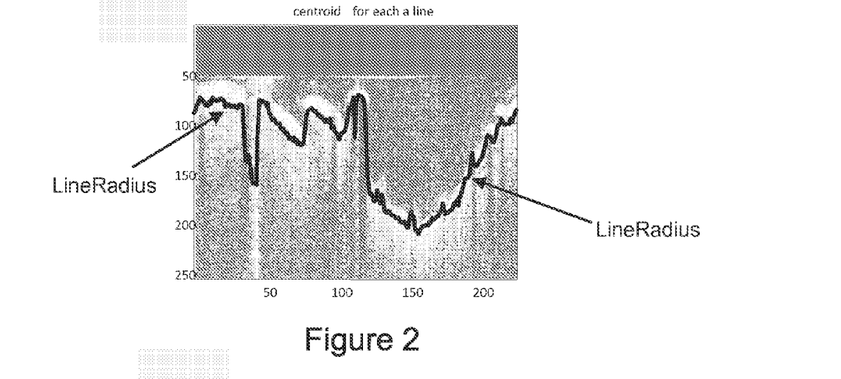
FIG. 2 is a rectangular (non-polar) representation of a cross-section of a lumen generated using data collected using an OCT probe such that certain LineRadius values are plotted according to an illustrative embodiment of the invention.

FIG. 2 is a rectangular (non-polar) representation of an OCT image with that shows the LineRadius (or line radius) values as calculated in the first step of the compute radius metric process. In one embodiment, the first step is computing a LineRadius for each rotation angle of the probe within a frame. As an example, certain line radius values are plotted according to an illustrative embodiment of the invention in FIG. 2. In one embodiment, to compute each LineRadius value, the intensity centroid of each line is calculated as follows (where cr is the catheter radius and n is the number of reduced samples per line, and i is the line number, i ranging from 1 to m):

$$LineRadius_i = \frac{\sum_{k=cr}^{n} Intensity_{i,k}(k-cr)}{\sum_{k=cr}^{n} Intensity_{i,k}}$$

Thus, the use of a LineRadius value provides a method for calculating a close approximation for actual physical radius of a vessel, and depends on (as mentioned previously) the unique characteristics of the OCT signal. Here the signal intensity, in the cleared vessel, is highly localized near the vessel wall due to the rapid attenuation of the OCT signal with distance into tissue. The position of the centroid of this signal (the 'LineRadius') will occur a small distance inside the vessel wall, not exactly on the vessel surface. Conventional edge finding techniques would localize the radius on the physical surface but come at the expense of much more computationally intensive process. Thus, the use of intensity as a proxy or surrogate for a physical radius dramatically improves the OCT system's ability to quickly determine a lumen radius or cross-sectional shape. Various intensity distribution moments can be compared to determine parameters of interest such as position and quality metrics.

Hence, this LineRadius value is computationally efficient (one multiplication and two running sums), but does not attempt to localize the actual lumen boundary with high precision at the vessel surface. Thus, it is not suitable for accurately measuring a conventional lumen diameter, but provides an excellent estimate of the cleared area. Another innovative step is to calculate a smooth fitting of the LineRadii using a fairly low-order harmonic series (shown below).

$$J \equiv \sum_{i=0}^{m} \left( LineRadius_i - \left( B_0 + \sum_{r=1}^{p} \left( \left( A_r \sin\left(\frac{2\pi ri}{m}\right) \right) + B_r \cos\left(\frac{2\pi ri}{m}\right) \right) \right) \right)^2$$

J is minimized over the A and B parameters, m is the number of lines per image frame (each image frame representing 360 degrees of catheter rotation), A and B are the weighting coefficients, and p is the harmonic order, typically 3 or less. The sine and cosine functions are used since, for a catheter off-center in an assumed round artery, the distance from the catheter center to the lumen edge as a function of rotation angle will follow a sinusoidal function. In one embodiment, the order of the curve fitting series J or the series of sine and cosine functions defined therein is 5 or less. This data smoothing process efficiently removes artifacts unique to the OCT intravascular image, such as the shadow caused by a guidewire using in the OCT system.

The smoothed radius profile as a function of angle is then:

$$SmoothRadius_i \equiv B_0 + \sum_{r=1}^{p} \left( \left( A_r \sin\left(\frac{2\pi ri}{m}\right) \right) + \left( B_r \cos\left(\frac{2\pi ri}{m}\right) \right) \right)$$

Figure 3:
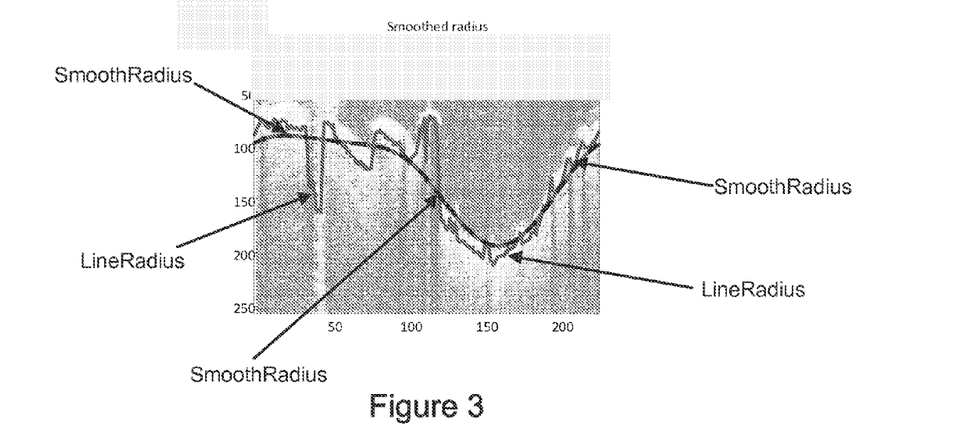
FIG. 3 is the same image as shown in FIG. 2 with the addition of a plotted curve that shows certain smooth radius values as determined using a method embodiment of the invention.

The effective clearing radius metric is the maximum of the SmoothRadii across all lines of the frame. This value is in samples, and represents the maximum radius of the clearing in samples outside the catheter. Examples of smooth radii values are shown in FIG. 3. FIG. 3 is the same image as shown in FIG. 2 with the addition of a plotted curve that shows certain smooth radius values SR as determined using the approach provided herein.

Compute Quality

Figure 4:
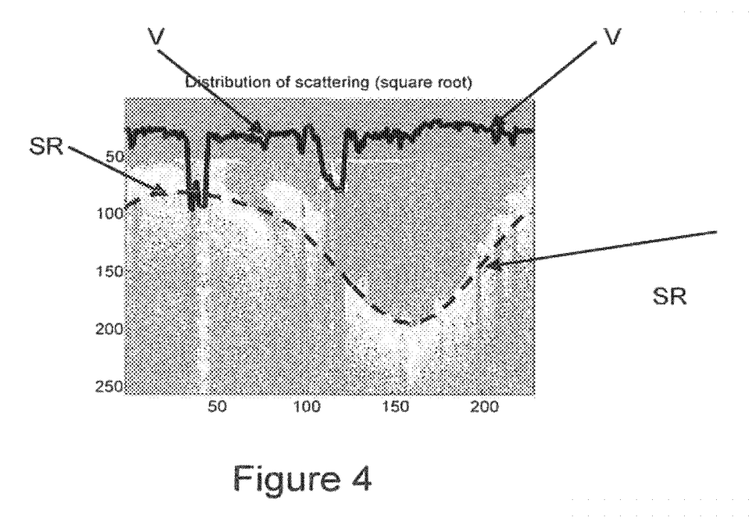
FIG. 4 is the same image as shown in FIGS. 2 and 3 with the addition of certain variance values as determined using a method embodiment of the invention.

Next, it is useful to consider the distribution of scattering about the vessel wall such as an artery wall as determined by the computer system. To do this, the software calculates a Variance, or distribution of scattering about the smooth radius, for each line of the frame as shown in FIG. 4. This is calculated as a mean-squared distribution for each line, as follows:

$$Variance = \frac{\sum_{k-cr}^{n} Intensity_{i,k}((k-cr) - SmoothRadius_i)^2}{\sum_{k-cr}^{n} Intensity_{i,k}}$$

If the intensity (signal) is localized very close to the smooth radius, the variance term will be small. A plot of variance values V is shown in FIG. 4. The quality metric can be calculated using the variance and the effective artery radius metric as follows:

$$Quality = \frac{\sqrt{mean(Variance)}}{Radius}$$

The unit for the quality metric (alternatively referred to as Quality) is dimensionless, and as the quality of the clearing in the image improves the value of this metric will decrease (lower quality metric value means better clearing). This simple variable again allows computationally efficient distinction of no clear, partial clear and fully clear situations as shown in the table below by amplifying the differences between distinguishing characteristics of the OCT images:

| Physical Condition | Variance | LineRadius | Quality Metric |
|---|---|---|---|
| No clearing - blood field | Low | Very Low | High (poor image) |
| Partial Clearing | High | Moderate | Moderate-high |
| Full Clear | Low | Large | Low |

Determine Clearing State

In one embodiment, there are two possible clearing states to be tested for once the Radius and Quality metric values have been calculated, the full clearing and the initial clearing states. In one embodiment, a single blood clear state is sufficient. When determining the clearing state for the current frame, the software resident in memory in the computer system connected to the probe detects if the image is in the full clearing state. This blood clearing state indicates that sufficient clearing has been detected in the image so that imaging of the artery or other vessel can begin. If the radius metric value for this frame is greater than the min radius setting, and the quality value is less than the max quality lower bound setting, then this frame is determined to be "fully clear." However, the full clearing state is not detected until the number of "fully clear" frames equals or exceeds the min frames setting. When all of these criteria have been met, the pullback will be triggered.

The second state, initial clearing, indicates that some amount of clearing has been detected in the image. If the radius metric value for this frame is greater than the init min radius setting, and the quality metric value is less than the initial max quality lower bound setting (>full clear lower bound), then this frame is "initially clear". However, the initial clearing state is not detected until the number of consecutive "initially clear" frames equals the init min frames setting. When initial clearing is detected the initial clearing timeout period is started, and if full clearing is not detected within that period then the pullback will be triggered.

Clinical Implementation

The above computer-based method is computationally efficient and effective at determining when scattering blood has been removed from an artery whose size, relative position to the imaging core of the catheter and relative shape are all unknown prior to clearing.

In one clinical implementation, another factor may be considered. Specifically, it is desirable to inject small boluses of saline or radio-opaque contrast agent ('contrast' or 'dye') during the course of the OCT data collection process. These dye shots typically range from about 5 ml to at most about 20 ml. The contrast agent shows the outline of the vessels in the fluoroscopic (x-ray) image to the interventional cardiologist or other OCT operator and is invaluable in guiding therapy (stent deployment, catheter location, etc.). Since contrast agent is optically clear, it is an effective flush agent. Thus, the OCT system must guard against these small dye shots producing false triggers as the bolus size is too small to produce a complete pullback OCT image of the vessel.

Accordingly, in one embodiment, the computer-based method is only 'armed' for triggering when either the system is enabled, signifying the next clearing event will be due to a bolus sized for OCT imaging, or by communication with an automated injector pump which has several injection sequences pre-programmed (e.g. 'dye shot' and 'OCT image data collection'). When an OCT image data collection injection is selected, the pump can communicate this to the OCT system, thereby arming the flush clearing detection methods and triggering methods. This communication can occur via several mechanisms, such as standard serial communication lines. Many modern injector pumps have this capability already existing as they facilitate a similar communication to the x-ray system.

Furthermore, through this communication set-up, clinical efficiency and patient safety can be enhanced. For example, it is desirable to limit exposure both to ionizing x-ray radiation (cell damage or mutation leading to cancer risk) and excessive contrast media as the radio-opaque material (typically iodine) is toxic in large quantities and is linked to renal insufficiency or outright renal failure. Hence by using a contrast agent as the flush agent, and synchronizing both the OCT image and the x-ray equipment, OCT and fluoroscopic images can be created simultaneously, neither degrading nor affecting the other. Contrast agent, due to its viscosity, allows smaller boluses and much lower flush rates than the volume for flushing with low-viscosity saline would require. As a result, using contrast agent as the flush offers additional patient safety advantages, as the high flush rates required by saline usage can be damaging to arterial walls. The computer-based method above is unaffected by the type of flush media used, as long as it is sufficiently optically clear at the OCT wavelength being used. In on embodiment, sufficient clearing occurs when the hematocrit level is reduced to the point that OCT images of sufficient quality for the intended clinical purpose can be made.

An alternative to the communication with the pump, especially if a manual (syringe) injection of flush media is used, is the use of a sterile pressure sensor in-line with the flush delivery mechanism. For example, a commercial disposable blood pressure transducer could be attached directly to the syringe used for flushing. The signal, from the transducer, would be detected similarly to the signal from the automated pump. Either signal can be used to control the OCT recording in one of two basic ways.

In the first way, smallest recording size, all image recording and pullback occurs simultaneously with the advent of a positive clearing signal from the computer-based method. In the second way, which produces a ~25% longer recording, the image recording starts when a flush signal is received (from either the pump or the transducer), but the pullback commences when the positive clearing signal is received. The resulting recording will indicate the stationary part of the scan and the portion during which pullback occurred. The advantage of the second method is that the recording captures the actual clearing and can be used to further refine the computer-based method.

Non-Limiting Software Features and Embodiments for Implementing OCT Methods and Systems The present invention may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. In a typical embodiment of the present invention, some or all of the processing of the data collected using an OCT probe and the processor-based system is implemented as a set of computer program instructions that is converted into a computer executable form, stored as such in a computer readable medium, and executed by a microprocessor under the control of an operating system. Thus, query response and input data are transformed into processor understandable instructions suitable for generating OCT data, triggering on a blood clearing state, using intensity to determine lumen geometry, histology images, OCT images, triggers, flush monitoring, signal processing, signal to noise evaluation in images, image comparison, signal processing, artifact removal, and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as OCT scan data, interferometer signal data, clock signals, region of interest types, formulas, and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the invention.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Furthermore, whereas particular embodiments of the invention have been described herein for the purpose of illustrating the invention and not for the purpose of limiting the same, it will be appreciated by those of ordinary skill in the art that numerous variations of the details, materials and arrangement of elements, steps, structures, and/or parts may be made within the principle and scope of the invention without departing from the invention as described in the claims.

The invention claimed is:

1. A computer-implemented method of triggering optical coherence tomographic data collection in a length of a vessel, the method comprising:
    collecting optical coherence tomography data with respect to a location in the vessel using an optical coherence tomography probe disposed in the vessel;
    determining, using a computer, a line radius for each rotation angle of the probe within a frame of the optical coherence tomography data to generate line radii;
    determining, using a computer, a smoothed radius profile of the vessel using the line radii;
    determining, using a computer, a parameter indicative of blood clearing in response to measured intensity values for one or more frames of optical coherence tomography data using a maximum smoothed radius value determined from the smoothed radius profile;
    determining if a blood clearing state has occurred using the parameter; and
    generating a trigger signal in response to the blood clearing state.

2. The computer-implemented method of claim 1, further comprising the step of triggering longitudinal optical coherence tomography data collection in response to the trigger signal.

3. The computer-implemented method of claim 2, wherein a time delay timeout occurs prior to commencing longitudinal optical coherence tomography data collection.

4. The computer-implemented method of claim 1, wherein the parameter is selected from the group consisting of vessel wall scattering, a vessel quality value, a vessel clearing radius, a plurality of vessel intensity values, LineRadius, quality metric, clearing radius, quality value, full clear frame and initial clear frame.

5. The computer-implemented method of claim 1 wherein the step of determining the parameter is performed using at least one intensity value or at least one intensity-derived position such that the intensity value is correlated with a boundary of the vessel.

6. The computer-implemented method of claim 5 wherein the at least one intensity value represents a position of a centroid of an intensity distribution along each radial line in at least one image generated from the optical coherence tomography data.

7. The computer-implemented method of claim 6 wherein the position of the centroid is within a wall of the vessel.

8. The computer-implemented method of claim 6 wherein the position of the centroid is determined using a computer performing the step of fitting a function of a plurality of radii using a series comprising sine and cosine functions.

9. The computer-implemented method of claim 8 wherein a maximum or minimum clearing radius is determined using the series.

10. The computer-implemented method of claim 1 further comprising collecting optical coherence tomographic data in response to the trigger signal.

11. The computer-implemented method of claim 1 wherein a clearing radius is determined by detecting scattering from a wall of the vessel.

12. The computer-implemented method of claim 1 wherein a quality value is a determined using scattering about a detected clear area of the vessel and a clearing radius.

13. The computer-implemented method of claim 1 wherein a quality factor is determined using a computer by a ratio of an intensity-position variance and maximum clear radius.

14. The computer-implemented method of claim 1 wherein the parameter is a quality metric determined using a computer by a ratio of an intensity standard deviation and maximum clear radius.

15. The computer-implemented method of claim 1 wherein the parameter is a quality metric determined using a computer by comparing a second moment of the intensity distribution to a first moment of the intensity distribution.

16. The method of claim 1 further comprising removing a shadow of a guidewire, wherein the guidewire is disposed in the vessel.

17. A computer system for triggering optical coherence tomography data collection, the computer system comprising:
an electronic memory device and
an electronic processor in communication with the memory device, wherein the memory device comprises instructions that when executed by the processor cause the processor to:
receive optical coherence tomography data with respect to a vessel;
determine a line radius for each rotation angle of a probe within a frame of the optical coherence tomography data to generate line radii;
determine a smoothed radius profile of the vessel using the line radii;
determine, a parameter indicative of blood clearing in response to measured intensity values for one or more frames of optical coherence tomography data using a maximum smoothed radius value determined from the smoothed radius profile;
determine if a blood clearing state has occurred based on the parameter; and
generate a trigger signal in response to the blood clearing state.

18. The computer system of claim 17 wherein the instructions further cause the processor to initiate optical coherence tomography data collection and pullback of an optical coherence probe in response to the trigger signal.

19. The computer system of claim 17 wherein the instructions further cause the processor to initiate a pullback of an optical coherence probe through the vessel.

20. The computer system of claim 17 wherein the processor determines the parameter using at least one intensity value such that the intensity value is correlated with a boundary of the vessel.

21. The computer system of claim 17 wherein the processor determines the parameter using scattering of light from a wall of the vessel.

22. The computer system of claim 17 wherein the blood clearing state is determined by detecting an initial clearing state or a full clearing state.

23. An optical coherence tomography data collection system comprising:
a processor; and
an optical coherence tomography probe comprising a rotatable optical fiber, wherein the processor is programmed to
determine a line radius for each rotation angle of the probe within a frame of the optical coherence tomography data to generate line radii;
determine a smoothed radius profile of a blood vessel using the line radii;
determine if a blood clearing state has occurred based on the smoothed radius profile;
trigger a pullback of the optical coherence tomography probe through the blood vessel in response to the blood clearing state based on a blood clearing parameter.

24. The optical coherence tomography data collection system of claim 23 wherein the blood clearing parameter is selected from the group consisting of vessel wall scattering, a vessel quality value, a vessel clearing radius, a plurality of vessel intensity values, LineRadius, and quality metric.

25. The optical coherence tomography data collection system of claim 23 wherein the blood clearing parameter is a clearing radius determined in response to an intensity of a wall of the vessel.

26. The optical coherence tomography data collection system of claim 23 wherein the processor collects data from the rotatable optical fiber during at least a portion of the pullback.

27. The optical coherence tomography data collection system of claim 23 wherein the vessel is a coronary artery.

28. The optical coherence tomography data collection system of claim 23 wherein the processor is programmed to initiate the pullback if a quality metric has reached a predetermined threshold.

29. The optical coherence tomography data collection system of claim 23 wherein the processor determines if the blood clearing state has occurred on a frame by frame basis.

* * * * *